(12) United States Patent
Jordanova-Spassova

(10) Patent No.: US 6,881,227 B2
(45) Date of Patent: *Apr. 19, 2005

(54) HYDROXYLAPATITE MATERIAL CONTAINING TRICALCIUM PHOSPHATE WITH MICROPOROUS STRUCTURE

(76) Inventor: Margarita Jordanova-Spassova, Boul, Petroko Todorov, B1 3, Eing, A: App. 10, 1404 Sofia (BG)

( * ) Notice: Subject to any disclaimer, the term of this patent is extended or adjusted under 35 U.S.C. 154(b) by 313 days.

This patent is subject to a terminal disclaimer.

(21) Appl. No.: 10/121,642

(22) Filed: Apr. 12, 2002

(65) Prior Publication Data

US 2002/0114755 A1 Aug. 22, 2002

Related U.S. Application Data

(63) Continuation-in-part of application No. 09/451,691, filed on Nov. 30, 1999, now Pat. No. 6,428,803.

(30) Foreign Application Priority Data

Oct. 13, 2000 (EP) ................. PCT/EP00/10117

(51) Int. Cl.$^7$ ............................ A61F 2/28; C01B 25/32
(52) U.S. Cl. .................... 623/16.11; 423/308; 423/309; 423/311; 424/426
(58) Field of Search ................. 423/308, 309, 423/311; 623/16.11; 424/426

(56) References Cited

U.S. PATENT DOCUMENTS

| | | | | | |
|---|---|---|---|---|---|
| 3,929,971 | A | | 12/1975 | Roy | |
| 4,207,306 | A | * | 6/1980 | Jarcho | 423/594 |
| 4,861,733 | A | * | 8/1989 | White | 423/305 |
| 4,938,938 | A | * | 7/1990 | Ewers et al. | 423/311 |
| 4,976,736 | A | * | 12/1990 | White et al. | 501/1 |
| 5,783,217 | A | | 7/1998 | Lee | |
| 6,024,985 | A | | 2/2000 | Simkiss | |
| 6,428,803 | B1 | * | 8/2002 | Ewers et al. | 623/16 |

FOREIGN PATENT DOCUMENTS

| | | |
|---|---|---|
| DE | 35 42 744 B1 | 5/1987 |
| DE | 37 09 897 B1 | 10/1988 |
| WO | WO 98-54089 B1 | 12/1998 |

OTHER PUBLICATIONS

Database WPI. Section Ch. Week 198445.Derwent Publications Ltd., London, GB, AN 1984–278946, XPOO2158583 & JP 59 171545 A (Yoshida Seisakusho KK) Sep. 28, 1984—Abstract.

* cited by examiner

*Primary Examiner*—Wayne A. Langel
(74) *Attorney, Agent, or Firm*—Pepper Hamilton LLP

(57) ABSTRACT

The invention relates to a hydroxylapatite material containing phosphate wherein the microporous structure of algae hard-tissue raw material is retained in the end product and which can be obtained by reacting an organic compound devoid of algae hard-tissue in an alkaline aqueous phosphate solution by adding magnesium ions at an elevated temperature. The invention also relates to a method for the production of said hydroxylapatite material containing tricalcium phosphate, which is characterized in that it is especially well resorbed in the body, is especially suitable as a bone substitute material or as a carrier material for active ingredients. Said material can also be used as a filter material.

24 Claims, No Drawings

HYDROXYLAPATITE MATERIAL CONTAINING TRICALCIUM PHOSPHATE WITH MICROPOROUS STRUCTURE

RELATED APPLICATIONS

This application claims priority to the pending International Patent Application Number PCT/EP00/10117, which was filed Oct. 13, 2000, which designates the United States as a designated state, and which also claims priority to German patent application number DE 199 50 113 0, filed Oct. 18, 1999. This application is also a continuation-in-part of, and claims priority to, pending U.S. patent application Ser. No. 09/451,691, filed Nov. 30, 1999 U.S. Pat. No. 6,428,803. Both the pending PCT application and the pending U.S. application referenced above are incorporated by reference into this patent application in their entirety.

FIELD OF THE INVENTION

The present invention relates to a hydroxylapatite material containing tricalcium phosphate, a process for its production and use of the hydroxylapatite material in the field of bone surgery and as a filter material.

BACKGROUND OF THE INVENTION

In the field of bone surgery there is a need for bone replacement materials and implants which are compatible with the human body and easy to work with. To facilitate its growth in the body the bone implant should have a structure which is as similar as possible to that of bone. The implant material should thus be suitable as media for materials such as growth-promoting or growth-inhibiting substances, for example.

U.S. Pat. No. 3,929,971, to Roy, discloses synthetic materials which should likewise be made from the skeleton of corals, whereby it is proposed to design the process such that the resulting microstructure of corals mainly comprises either tricalcium phosphate (whitlockite) or hydroxylapatite.

A hydroxylapatite material, obtained from the calcium carbonate skeleton of lime-encrusting algae, has thoroughly proven itself as bone replacement material. Such a material is described in German Patent Number DE 37 09 897 C2, to Ewers et al. In order to mask the magnesium naturally present in the algae and to prevent the formation of β-tricalcium phosphate during production of hydroxylapatite material, fluoride is preferably added to the reaction mixture. For producing moulded articles the granular hydroxylapatite material obtained by hydrothermal synthesis is vibrated with dissolved lime as binder into a moulded article and then again subjected to hydrothermal treatment. The resulting bone implant has high interconnective porosity and a high specific surface. In its chemistry and crystalline structure it is substantially more similar to bones than other bone replacement materials.

Despite the excellent properties of the hydroxylapatite material described in German Patent Number DE 37 09 897 C2, to Ewers et al., it is desirable to have a bone replacement material available whose resorption in the organism is further improved and which leads to even faster formation of new bone. It has eventuated that hydroxylapatite material already has relatively good biological properties when supplied in the body, but that a lengthy biological decomposition has to be taken into consideration. This fact, in particular for hydroxylapatite materials with crystal sizes of the order of several micrometers with a Ca/P ratio of 1.67, is known from International Patent Application Number WO 97/17285 A1, from which issued U.S. Pat. No. 5,783,217, to Lee et al., and also from International Patent Application Number WO 94/02412 A1, from which issued U.S. Pat. No. 6,024,985, to Simkiss et al. But also for the hydroxylapatite materials known from German Patent Number DE 37 09 897 C2, to Ewers et al., in which the interconnective pore structure of the lime-encrusting algae remains intact, the biological decomposition period is greater than with tricalcium phosphate, for example. On the other hand, the biological decomposition period of tricalcium phosphate is substantially shorter. Most desirable is a biological decomposition period which is synchronised approximately with time, with which the bone regrows in place of the degraded bone replacement material. This results in the requirement for bone replacement material, where the decomposition period can be adjusted at least within certain limits during manufacture, thus stimulating accelerated bone formation without the material degrading too rapidly and accordingly without an interim period filled with connective tissue, for example, resulting.

OBJECTS OF THE INVENTION

An object of the present invention is to provide a bone replacement material which has a high interconnective pore structure, is very compatible with the body and has improved and controllable resorption in the organism, thus resulting in accelerated bone formation. The bone replacement material should also be suitable as media for materials such as for example growth-promoting or growth-inhibiting substances.

Further objects of the inventions will become evident in the description below.

SUMMARY OF THE INVENTION

The solution to this problem is the hydroxylapatite material containing tricalcium phosphate with a microporous structure, obtained by converting a hard algae tissue free of organic compounds in an alkaline aqueous phosphate solution with addition of $Mg^{2+}$ ions at increased temperature, wherein the microporous structure of the hard algae tissue starting materials remains intact in the hydroxylapatite material, and wherein the material has a tricalcium phosphate content of 50 to 90% by weight. The invention further relates to a process for producing such a hydroxylapatite material containing tricalcium phosphate, wherein a hard algae tissue free of organic compounds is converted in an alkaline aqueous phosphate solution with the addition of a water-soluble magnesium salt at increased temperature.

The hydroxylapatite material containing tricalcium phosphate according to the present invention is distinguished by a tricalcium phosphate content which is substantially greater than that of a hydroxylapatite material obtained in a conventional manner from lime-encrusting algae.

The β-tricalcium phosphate (β-whitlockite) content of hydroxylapatite material, obtained from lime-encrusting algae, depends on the quantity of magnesium ions which are present during production of the hydroxylapatite material. As mentioned at the outset, naturally occurring algae have a certain magnesium content. This natural magnesium content in algae is normally ca. 2.5%, and in exceptional cases is also as much as approximately 6% by weight. This leads to a content of up to 10% by weight, in exceptional cases also as much as approximately 20% by weight, β-tricalcium phosphate in a hydroxylapatite material produced according to DE 37 09 897 C2 from these algae. It should be noted that magnesium is present in the algae in a form bound at least partially in the structure, namely predominantly in the form of $MgCO_3$, $MgO$ and $(Ca, Mg)CO_3$, which obviously results in not only β-tricalcium phosphate being produced with this magnesium, but also other, disturbing phases being produced with a magnesium portion. The drawback apparent in DE 37 09 897 C2 was that tricalcium phosphate develops during the production of the hydroxylapatite material. For this reason in a preferred production variant the magnesium naturally present in the algae starting material is masked by concentrated addition of fluoride ions to suppress development of tricalcium phosphates.

The knowledge underlying the invention is that a hydroxylapatite material with a tricalcium phosphate content, which is higher than that content automatically adjusted with use of a specific type of algae, is improved with respect to resorption in the organism and new bone formation compared to conventional hydroxylapatite material, without worsening of the other beneficial properties. This increased tricalcium phosphate content is achieved by concentrated addition of magnesium ions during production of the material.

The invention thus relates to a hydroxylapatite material containing tricalcium phosphate, obtainable by conversion of a hard algae tissue free of organic compounds in an alkaline aqueous phosphate solution with addition of magnesium ions at increased temperature. Adding the magnesium ions augments the magnesium content in the reaction mixture above the level corresponding to the natural magnesium content of the corresponding type of algae used as starting material of the synthesis. The tricalcium phosphate content in the thus manufactured hydroxylapatite material correspondingly also increases.

According to the present invention it is possible through concentrated addition of magnesium ions to the reaction mixture to adjust the tricalcium phosphate content in the end product to a predetermined value. The tricalcium phosphate content in the hydroxylapatite material according to the present invention is preferably between 50 and 90% by weight.

To achieve a corresponding tricalcium phosphate content in hydroxylapatite material, it is conceivable to add 0.1 to ca. 15% by weight of magnesium ions in the form of a magnesium salt to the mixture of the solid starting materials (hard algae tissue and phosphate salt). Addition of the magnesium ions may not exceed 15% by weight, as otherwise an excessive quantity of other undesired phases containing magnesium, such as β-dittmarite ($MgNH_4PO_4 \cdot 6H_2O$) develops. For the hydroxylapatite material containing tricalcium phosphate having a microporous structure corresponding to the hard algae tissue according to the present invention the $Mg^{2+}$ contents in the mixture of the solid starting materials should be between 0.75 and 6% by weight.

As already mentioned, the hydroxylapatite material containing tricalcium phosphate according to the present invention combines all the advantages which are already known from the material described in German Patent Number DE 37 09 897 C2, to Ewers et al. The hydroxylapatite material according to the present invention retains the microporous structure of the hard algae tissue used as starting material, and thus exhibits a very high interconnective porosity. Due to the considerable porosity the hydroxylapatite material according to the present invention can also be utilised ideally as filter material. The specific surface of the material is very high. The material is highly body-compatible and in its chemistry is similar to bone, thus making it ideally suited as bone replacement material. By means of the increased tricalcium phosphate content compared to the material known from German Patent Number DE 37 09 897 C2, to Ewers et al., it is resorbed even better by the organism and accelerates new bone formation. The tricalcium phosphate content and thus the resorptive properties can be adjusted precisely by concentrating the magnesium ions. With increasing tricalcium phosphate content resorption in the body is faster. Vice versa, a higher hydroxylapatite content retards resorption. The hydroxylapatite material according to the present invention is also ideally suited as medium for active ingredients such as for example growth-promoting or growth-inhibiting substances. Special examples are antibiotics, chemotherapeutics, tumor-inhibiting compounds and bone-inductive substances. Examples of bone-morphogenic proteins (bone morphogenic proteins, BMP) are bone-inductive substances.

DETAILED DESCRIPTION OF THE INVENTION

In a preferred embodiment according to the present invention the hydroxylapatite material containing tricalcium phosphate has a content of at least one active ingredient. This can either be worked into the hydroxylapatite material according to the present invention or into the bone replacement material made thereof, or it is present as a coating on a bone replacement material which was produced using the hydroxylapatite material containing tricalcium phosphate according to the present invention. The at least one active ingredient in a clinically active quantity is applied to the hydroxylapatite material or the bone replacement material or mixed therein.

Basically any hard algae tissue, already used to produce hydroxylapatite materials, can be used as hard algae tissue which is used as starting material for the hydroxylapatite material according to the present invention. Particularly suitable is hard algae tissue, obtained from lime-encrusting sea algae. Examples of these sea algae are the species Amphiroa Ephedra, Corallinacea or Codiacea. These algae are effectively macerated, therefore pyrolised for example for ca. a whole day at 700° C. and then granulated. The resulting hard algae tissue predominantly comprises calcium carbonate (ca. 95% by weight), while the remaining approximately 5% by weight are chiefly calcium oxide and magnesium oxide.

In the process according to the present invention for manufacturing a hydroxylapatite material containing tricalcium phosphate this hard algae tissue free of organic compounds is converted in an alkaline aqueous phosphate solution with the addition of a magnesium salt at increased temperature. The ratio of hard algae tissue and phosphate salt is selected in a manner known per se such that the ratio of calcium to phosphorous corresponds to the ratio in the hydroxylapatite. The ratio of calcium to phosphorous in the hydroxylapatite is approximately 1.67. If diammonium hydrogen phosphate is used as phosphate salt for example, the weight ratio of hard algae tissue to phosphate salt is usually in the region of 1:0.8 to 1:1.5, preferably 1:0.95 to 1:1. The weight ratio fluctuates somewhat depending on the calcium content of the hard algae tissue used.

With respect to the content in magnesium ions in the reaction mixture the present case can be referred to. The magnesium salt is added in such a quantity that the tricalcium phosphate content in the end product is between 50 and 90% by weight. Magnesium nitrate is used as a preferred source of magnesium ions. However, other water-soluble magnesium salts can also be used. Diammonium hydrogen phosphate acts as a preferred phosphate compound, as already explained. The process according to the present invention is not limited to this salt, however.

The abovementioned reaction constituents are converted in an alkali at increased temperature. A preferred pH range is one between 8 and 11. Conversion takes place particularly effectively at a pH value between 9 and 9.5. All water-soluble bases can be used to adjust the pH value. Ammonia is particularly preferred.

An appropriate temperature range for carrying the process according to the present invention into effect is between 150 and 250° C., in particular between 200 and 250° C. A particularly preferred temperature range is between 230 and 250° C. At this temperature conversion will usually last at least 24 hours.

The process according to the present invention is carried out effectively at increased pressure. It has proved particularly suitable to perform the conversion in an autoclave. Preferably an autoclave provided with an inert coating is used. An autoclave sheathed in polytetrafluorethylene is particularly suitable.

It is particularly preferred to perform the hydrothermal conversion for the hydroxylapatite material containing tricalcium phosphate according to the present invention at the saturation steam pressure of the reaction solution. So that the saturation steam pressure can be adjusted during conversion, the autoclave is effectively filled to a maximum two thirds capacity.

EXAMPLES

The invention will now be described in greater detail hereinbelow with reference to examples.

Example 1

Production of the hydroxylapatite material containing tricalcium phosphate according to the present invention (a) A hard algae material of the species Corallina officinalis obtained by maceration of algae is poured in the form of a granulate with a grain size of over 0.5 mm into an autoclave lined with polytetrafluorethylene. Phosphate is added to the autoclave in such a quantity that the ratio of calcium to phosphorous in hydroxylapatite is in the range of 1.67. $(NH_4)_2HPO_4$ is used as phosphate salt. The weight ratio of hard algae tissue to phosphate salt is 1:0.95. The phosphate salt is added in the form of an aqueous solution, whereby the weight ratio of phosphate salt to water is approximately 1:4. Then magnesium is added to the autoclave in the form of von $Mg(NO_3)_2 \cdot 6H_2O$. The quantity is 2.5% by weight magnesium, relative to the solids content in the autoclave.

(b) By adding ammonia to the reaction mixture the pH value is adjusted to a value between 9 and 9.5. It should be noted that the autoclave is filled to no more than two thirds capacity.

(c) The hydrothermal conversion is carried out at a temperature between 230 and 250° C. for at least 24 hours. Conversion happens at the saturation steam pressure of the solution.

(d) When the hydrothermal reaction is completed the autoclave is cooled down. Next the pH value is regulated. If the pH value is no longer in the range set at the commencement of reaction, the reaction mixture is rejected. If the pH value is in the desired range, the aqueous phase is separated and rejected. The isolated hydroxylapatite material containing tricalcium phosphate is washed several times with warm distilled water and briefly boiled if required. After being washed the resulting hydroxylapatite material containing tricalcium phosphate is dried in an oven at a temperature of up to 200° C.

Example 2

Production of the hydroxylapatite material containing tricalcium phosphate according to the present invention The procedural steps (a), (b) and (d) correspond to Example 1 though synthesis is performed in a temperature range of 200° C to 240° C. The temperature in this arrangement varies, whereby synthesis first runs for two hours at a temperature of 200° C. Then the temperature for the next two hours is raised to 240° C, then readjusted to 200° C. This cycle is again maintained for a total of 24 hours. The change in temperature in the abovementioned limits leads to a high, but at the same time very fine crystal unity of the product. Both phases (hydroxylapatite and tricalcium phosphate) form very different crystallites, also with very different sizes. The tricalcium phase forms much larger crystallites than the apatite phase. If these crystallisation processes were left to run free, that is, at a constant temperature, these differences in the formation of both phases could well lead to destruction of the valuable microstructure of the algae skeleton. The partitions in the channel system of the skeleton are constructed namely of different conglomerates, resulting in destabilising of the structure in the event of inadequate processing parameters. Conversion takes place again with saturation steam pressure of the solution.

The change in the sintering temperature during the entire cycle alters the thermodynamic conditions in the autoclave, so that the crystallisation processes are completed, but the growth of the crystallites is relented and these remain small in the end. This is a process designed to create stability of the algae skeleton.

The following can be established as the result of this design. In a conventional synthesis cycle the tricalcium phosphate phase has a crystallite size of 100 to 150 nm and the apatite phase has a crystallite size of ca. 50 nm. According to Example 2 given here a crystallite size of 30 nm can be achieved for the apatite phase and for the tricalcium phosphate phase a size of 40 to 45 nm.

As an alternative embodiment the temperature of the hydrothermal synthesis can also be varied every four hours between 200° C. and 240° C.

The highest concentration of tricalcium phosphate in the product according to the present invention is ca. 90%, whereby the rest is mainly hydroxylapatite. The structure is stable and the individual kernels of the granulate are sufficiently hard. The maximum Mg addition is 5.5 to 6.0% by weight, calculated on the quantity of the distilled algae (calcite hard tissue). At a desired concentration of 50% tricalcium phosphate (at ca. 50% hydroxylapatite) addition is ca. 0.75% by weight, and at a desired concentration of 60% it is ca. 3.0% by weight. There is thus a jump with respect to the addition of Mg, which is necessary to achieve a concentration of tricalcium phosphate of clearly more than 50%. Such a concentration can be achieved with the above-described particularly suitable method of temperature variation. With very high proportions of tricalcium phosphate in the hydroxylapatite mass, for whose production the upper limit of the abovementioned magnesium quantity is used, crystalline forms of deposits with a magnesium portion inter alia of β-dittmarite (MgNH$_4$PO$_4$·6H$_2$O) can be avoided, in that the product is washed several times with weak acetic acid and bidistilled aqua.

The function of a catalyst is thus imparted to the excess quantity magnesium, otherwise required for reaction, which does not have the natural portion of magnesium in the distilled algae in the form of MgCO$_3$, MgO and (Ca, Mg)CO$_3$ bound in the crystal network.

With this invention has been described with reference to certain specific embodiments and examples, it will be recognized by those skilled in the art that many variations are possible without departing from the scope and spirit of this invention, and that the invention, as described by the claims, is intended to cover all changes and modifications of the invention which do not depart from the spirit of the invention.

What is claimed is:

1. A hydroxylapatite material containing tricalcium phosphate, obtained by converting a hard algae tissue free of organic compounds in an alkaline aqueous phosphate solution with addition of Mg$^{2+}$ ions at increased temperature, wherein the microporous structure of the hard algae tissue starting materials remains intact in the material, and the material has a tricalcium phosphate content of 50 to 90% by weight, wherein the reaction temperature is between 230 and 250° C.

2. The hydroxylapatite material containing tricalcium phosphate as set forth in claim 1, with a tricalcium phosphate content of 70 to 90% by weight.

3. The hydroxylapatite material containing tricalcium phosphate as set forth in claim 1, wherein said hard algae tissue is obtained from lime-encrusting sea algae.

4. The hydroxylapatite material as claimed in claim 1, comprising at least one active ingredient.

5. The hydroxylapatite material as claimed in claim 4, wherein at least one of the active ingredient(s) comprises either a growth promoting compound or a growth inhibiting compound.

6. The hydroxylapatite material as claimed in claim 4, wherein at least one of the active ingredient(s) comprises an antibiotic, a chemotherapeutic, a tumor inhibiting compound, or a bone morphogenic protein.

7. A process for producing a hydroxylapatite material containing tricalcium phosphate obtained by converting a hard algae tissue free of organic compounds in an alkaline aqueous phosphate solution with addition of Mg$^{2+}$ ions in the form of a water-soluble magnesium salt at increased temperature, wherein the microporous structure of the hard algae tissue starting materials remains intact in the processed material, and the material has a tricalcium phosphate content of 50 to 90% by weight, wherein the reaction temperature is between 230 and 250° C.

8. The process as claimed in claim 7, wherein the water-soluble magnesium salt is magnesium nitrate.

9. The process as claimed in claim 7, wherein said magnesium salt is added in such quantity that a content of 50 to 90% by weight tricalcium phosphate is obtained in the processed material.

10. The process as claimed in claim 9, wherein said magnesium salt is added in a quantity of 5.5 to 6.0% by weight.

11. The process as claimed in claim 7, wherein (NH$_4$)$_2$HPO$_4$ is used as phosphate.

12. The process as claimed in claim 7, wherein said conversion is carried out at a pH value between 8 and 11.

13. The process as claimed in claim 12, wherein the pH value is adjusted with NH$_3$.

14. A process for producing a hydroxylapatite material containing tricalcium phosphate obtained by converting a hard algae tissue free of organic compounds in an alkaline aqueous phosphate solution with addition of Mg$^{2+}$ ions in the form of a water-soluble magnesium salt at increased temperature, wherein the microporous structure of the hard algae tissue starting materials remains intact in the processed material, and the material has a tricalcium phosphate content of 50 to 90% by weight, wherein the reaction temperature is varied between 200 and 240° C.

15. The process as claimed in claim 14, wherein the reaction temperature is maintained respectively in cycles of ca. 200° and ca. 240° C.

16. The process as claimed in claim 15, wherein said cycles are two hours for each said temperature.

17. The process as claimed in claim 14, wherein said conversion is carried out at increased pressure.

18. The process as claimed in claim 15, wherein said conversion takes place in an autoclave coated with polytetrafluorethylene.

19. The process as claimed in claim 18, wherein said autoclave is filled to a maximum two thirds of capacity.

20. A hydroxylapatite material containing tricalcium phosphate, obtained by converting a hard algae tissue free of organic compounds in an alkaline aqueous phosphate solution with addition of Mg$^{2+}$ ions at increased temperature, wherein the microporous structure of the hard algae tissue starting materials remains intact in the material, and the material has a tricalcium phosphate content of 70 to 90% by weight, wherein the reaction temperature is varied in cycles between 200 and 240° C.

21. The hydroxylapatite material containing tricalcium phosphate as set forth in claim 20, wherein said hard algae tissue is obtained from lime-encrusting sea algae.

22. The hydroxylapatite material as claimed in claim 20, comprising at least one active ingredient.

23. The hydroxylapatite material as claimed in claim 22, wherein at least one of the active ingredient(s) comprises either a growth promoting compound or a growth inhibiting compound.

24. The hydroxylapatite material as claimed in claim 22, wherein at least one of the active ingredient(s) comprises an antibiotic, a chemotherapeutic, a tumor inhibiting compound, or a bone morphogenic protein.

* * * * *